(12) United States Patent
Niculescu-Mizil et al.

(10) Patent No.: US 9,449,284 B2
(45) Date of Patent: Sep. 20, 2016

(54) METHODS AND SYSTEMS FOR DEPENDENCY NETWORK ANALYSIS USING A MULTITASK LEARNING GRAPHICAL LASSO OBJECTIVE FUNCTION

(71) Applicant: NEC Laboratories America, Inc., Princeton, NJ (US)

(72) Inventors: Alexandru Niculescu-Mizil, Plainsboro, NJ (US); Diane Oyen, Santa Fe, NM (US)

(73) Assignee: NEC Corporation (JP)

( * ) Notice: Subject to any disclaimer, the term of this patent is extended or adjusted under 35 U.S.C. 154(b) by 166 days.

(21) Appl. No.: 14/049,891

(22) Filed: Oct. 9, 2013

(65) Prior Publication Data
US 2014/0101078 A1    Apr. 10, 2014

Related U.S. Application Data

(63) Continuation-in-part of application No. 14/046,460, filed on Oct. 4, 2013, now abandoned.

(60) Provisional application No. 61/709,532, filed on Oct. 4, 2012.

(51) Int. Cl.
| | |
|---|---|
| *G06F 15/18* | (2006.01) |
| *G06N 99/00* | (2010.01) |
| *G06N 7/00* | (2006.01) |
| *G06F 19/12* | (2011.01) |

(Continued)

(52) U.S. Cl.
CPC ............ G06N 99/005 (2013.01); G06N 7/005 (2013.01); *G06F 19/12* (2013.01); *G06F 19/20* (2013.01); *G06F 19/26* (2013.01)

(58) Field of Classification Search
CPC ....... G06N 7/005; G06N 3/08; G06K 9/6296
USPC ................................................. 706/12, 45
See application file for complete search history.

(56) References Cited

U.S. PATENT DOCUMENTS

| | | | | |
|---|---|---|---|---|
| 7,421,380 | B2 * | 9/2008 | Thiesson | ............ G06K 9/00523 |
| | | | | 702/182 |
| 7,596,475 | B2 * | 9/2009 | Thiesson | .............. G06K 9/6296 |
| | | | | 703/2 |
| 8,306,752 | B1 * | 11/2012 | Gardner | .................. G06F 19/24 |
| | | | | 435/6.1 |

(Continued)

OTHER PUBLICATIONS

Honorio et al.,Simultaneous and Group-Sparse Multi-Task Learning of Gaussian Graphical ModelsJul. 2012, pp. 1-25.*

(Continued)

*Primary Examiner* — David Vincent
(74) *Attorney, Agent, or Firm* — Joseph Kolodka

(57) ABSTRACT

Methods and systems for displaying dependencies within data and illustrating differences between a plurality of data sets are disclosed. In accordance with one such method, a plurality of data sets are received for the generation of a plurality of dependency networks in accordance with a graphical modeling scheme. The method further includes receiving a selection of a value of a parameter that adjusts a number of differences between the dependency networks in accordance with the graphical modeling scheme. In addition, at least one version of the dependency networks is generated based on the selected value of the parameter. Further, the one or more versions of the dependency networks is output to permit a user to analyze distinctions between the dependency networks.

20 Claims, 7 Drawing Sheets

(51) Int. Cl.
G06F 19/20 (2011.01)
G06F 19/26 (2011.01)

(56) References Cited

U.S. PATENT DOCUMENTS

| | | | | |
|---|---|---|---|---|
| 2006/0088207 A1* | 4/2006 | Schneiderman | ... | G06K 9/00241 382/159 |
| 2006/0287842 A1* | 12/2006 | Kim | ........................ | G01H 9/004 702/183 |
| 2007/0244682 A1* | 10/2007 | Ott | .......................... | G06F 19/12 703/11 |
| 2011/0022369 A1* | 1/2011 | Carroll | ...................... | G06N 3/02 703/11 |
| 2012/0122730 A1* | 5/2012 | Tran | ........................ | C40B 30/08 506/11 |
| 2013/0197875 A1* | 8/2013 | Shirley | ............ | G01R 31/31718 703/2 |
| 2013/0259847 A1* | 10/2013 | Vishnudas | .............. | G06F 19/12 424/94.1 |
| 2013/0315885 A1* | 11/2013 | Narain | .................... | G06F 19/12 424/94.1 |

OTHER PUBLICATIONS

Liu et al., Learning Temporal Causal Graphs for Relational Time-Series Analysis, 2010, Proceedings of the 27th International Conference on Machine Learning, pp. 1-8.*
Bergmann, S., et al. "Similarities and Differences in Genome-Wide Expression Data of Six Organisms" PLoS Biology, Comparative Analysis of Expression Data. vol. 2, No. 1. Jan. 2004. pp. 0085-0093.
Burge, J., et al. "Learning Class-Discriminative Dynamic Bayesian Networks" Proceedings of the 22nd International Conference on Machine Learning. ACM International Conference Proceeding Series. Aug. 2005. (8 Pages).
Chiquet, J., et al. "Inferring Multiple Graphical Structures" Statistics and Computing. vol. 21, No. 1. Jun. 2010. pp. 537-553.
Choi, B., et al. "Secretory Leukocyte Protease Inhibitor Is Associated With MMP-2 and MMP-9 to Promote Migration and Invasion in SNU638 Gastric Cancer Cells" International Journal of Molecular Medicine. vol. 28. May 2011. pp. 527-534.
Clark, V., et al. "TDCS Guided Using FMRI Significantly Accelerates Learning to Identify Concealed Objects" NeuroImage, vol. 59, No. 1. Nov. 2010. pp. 117-128.
Danaher, P., et al. "The Joint Graphical Lasso for Inverse Covariance Estimation Across Multiple Classes" Journal of the Royal Statistical Society: Series B (Statistical Methodology). Nov. 2011. (27 Pages).
De La Fuente, A. "From 'Differential Expression' to 'Differential Networking'—Identification of Dysfunctional Regulatory Networks in Diseases" Trends in Genetics, vol. 26, No. 7. 2010. pp. 326-333.
Gold, L., et al. "Aptamer-Based Multiplexed Proteomic Technology for Biomarker Discovery" PLoS One, Aptamer-Based Proteomics. vol. 5. No. 12. Dec. 2010. pp. 1-17.
Grossman, D., et al. "Learning Bayesian Network Classifers by Maximizing Conditional Likelihood" Proceedings of the 21st International Conference on Machine Learning. Jul. 2004. (8 Pages).
Guo, J., et al. "Joint Estimation of Multiple Graphical Models" Biometrika. vol. 98., No. 1. Feb. 2011. (15 Pages).
Guo, J., et al. "Joint Estimation of Multiple Graphical Models" Department of Statistics, University of Michigan, Ann Arbor. Apr. 2010. (31 Pages).
Hara, S., et al. "Learning a Common Substructure of Multiple Graphical Gaussian Models" Neural Networks. vol. 38. Nov. 2012. pp. 23-28.
Hirohashi, S., et al. "Cell Adhesion System and Human Cancer Morphogenesis" Cancer Sci. vol. 94, No. 7. Jul. 2003. pp. 575-581.
Honorio, J., et al. "Multi-Task Learning of Gaussian Graphical Models" Proceedings of the 27th International Conference on Machine Learning. Jun. 2010. (8 Pages).
Huang, D., et al. "Systematic and Integrative Analysis of Large Gene Lists Using David Bioinformatics Resources" Nature Protocols. vol. 4, No. 1. Dec. 2008. (43 Pages).
Liu, H., et al. "Stability Approach to Regularization Selection (Stars) for High Dimensional Graphical Models" Advances in Neural Information Processing Systems 23: 24th Annual Conference on Neural Information Processing Systems 2010. Dec. 2010. Pages 1-14.
Liu, H., et al. "Transelliptical Graphical Models" Advances in Neural Information Processing Systems 25: 26th Annual Conference on Neural Information Processing Systems 2012. Dec. 2012. pp. 1-9.
Lopez-Candales, A., et al. "Cholesterol Transport Function of Pancreatic Cholesterol Esterase: Directed Sterol Uptake and Esterification in Enterocytes" Biochemistry. vol. 32. Nov. 1993. pp. 12085-12089.
Meinshausen, N., et al. "High-Dimensional Graphs and Variable Selection With The Lasso" The Annals of Statistics. vol. 34, No. 3. Jun. 2006. pp. 1436-1462.
Mishkin, M., et al. "Object Vision and Spatial Vision:Two Cortical Pathways" Trends in Neuroscience. vol. 6. Oct. 1983. pp. 414-417.
Mohan, K., et al. "Structured Learning of Gaussian Graphical Models" 26th Annual Conference on Neural Information Processing Systems 2012. Dec. 2012. pp. 1-9.
Roy, S., et al. "A Multiple Network Learning Approach to Capture System-Wide Condition-Specific Responses" Bioinformatics. vol. 27, No. 13. May 2011. pp. 1832-1838.
Shannon, P., et al. "Cytoscape: a Software Environment for Integrated Models of Biomolecular Interaction Networks" Genome Research. vol. 13. Nov. 2003. pp. 2498-2504.
Smith, S., et al. "Network Modelling Methods for FMRI" NeuroImage, vol. 54, No. 1. Sep. 2010. pp. 875-891.
Tzourio-Mazoyer, N., et al. "Automated Anatomical Labeling of Activations in SPM Using a Macroscopic Anatomical Parcellation of the MNI MRI Single-Subject Brain" NeuroImage. vol. 15. Jan. 2002. pp. 273-289.
Varoquaux, G. et al. "Brain Covariance Selection: Better Individual Functional Connectivity Models Using Population Prior" 24th Annual Conference on Neural Information Processing Systems 2010. Dec. 2010. pp. 1-10.
Walker, G., et al. "Insulin-Like Growth Factor Binding Proteins IGFBP3, IGFBP4, and IGFBP5 Predict Endocrine Responsiveness in Patients With Ovarian Cancer" Clinical Cancer Research. vol. 13. Mar. 2007. pp. 1438-1444.
Zhang, B., et al. "Differential Dependency Network Analysis to Identify Condition-Specific Topological Changes in Biological Networks" Bioinformatics. vol. 25, No. 4. Dec. 2008. pp. 526-532.

* cited by examiner

METHODS AND SYSTEMS FOR DEPENDENCY NETWORK ANALYSIS USING A MULTITASK LEARNING GRAPHICAL LASSO OBJECTIVE FUNCTION

RELATED APPLICATION INFORMATION

This application is a Continuation-in-part application of co-pending U.S. patent application Ser. No. 14/046,460 filed on Oct. 4, 2013, which claims priority to Provisional Application Ser. No. 61/709,532 filed on Oct. 4, 2012. Both U.S. patent application Ser. No. 14/046,460 and Provisional Application Ser. No. 61/709,532 are incorporated herein by reference in their entireties.

BACKGROUND

1. Technical Field

The present invention relates to dependency networks, and, more particularly, to identifying and displaying differences between dependency networks.

2. Description of the Related Art

Network structure learning algorithms, such as Gaussian graphical models, enable scientists to visualize dependency structures in multivariate data. Recently, the problem of identifying differences in dependency networks among various classes of data has become increasingly important. For example, one neuroimaging study seeks to determine how regions of the brain share information before and after a person acquires a particular skill. The goal in this study is to identify the regions of the brain that are most influential after a skill has been learned so that direct current stimulation can be applied to those particular regions to accelerate a person's learning process. In another example, the differences between dependency structures of plasma proteins of patients that have cancer and of patients that do not have cancer have been studied to further understanding of cancer biology and to identify improved cancer diagnostics.

Traditional methods for differential dependency network analysis tend to produce a large number of spurious differences that significantly limits their usefulness. Typically, such methods are based on learning a dependency network for each task independently and then performing a comparison between them. However, large numbers of spurious differences hamper the analysis and prevent a determination of any reliable conclusions from the differential analysis. Further, these spurious differences are usually difficult to eliminate through follow-up tests.

SUMMARY

One exemplary embodiment is directed to a method for displaying dependencies within data and illustrating differences between a plurality of data sets. In accordance with the method, a plurality of data sets is received for the generation of a plurality of dependency networks in accordance with a graphical modeling scheme. The method further includes receiving a selection of a value of a parameter that adjusts a number of differences between the dependency networks in accordance with the graphical modeling scheme. In addition, at least one version of the dependency networks is generated based on the selected value of the parameter. Further, the one or more versions of the dependency networks is output to permit a user to analyze distinctions between the dependency networks.

Another exemplary embodiment is also directed to a method for displaying dependencies within data and illustrating differences between a plurality of data sets. In accordance with the method, the plurality of data sets is received for the generation of a plurality of dependency networks in accordance with a graphical modeling scheme. The method further includes receiving a first selection of a first value of a first parameter that adjusts a number of differences between the dependency networks in accordance with the graphical modeling scheme and receiving a second selection of a second value of a second parameter that adjusts a sparsity within at least one of the dependency networks in accordance with the graphical modeling scheme. In addition, at least one version of the plurality of dependency networks is generated based on the selected first value of the first parameter and on the selected second value of the second parameter. Further, the one or more versions of the plurality of dependency networks is output to permit a user to analyze distinctions between the dependency networks.

Another exemplary embodiment is directed to a system for displaying dependencies within data and illustrating differences between a plurality of data sets. The system includes a controller and a modeling unit. The controller is configured to receive the plurality of data sets for the generation of a plurality of dependency networks in accordance with a graphical modeling scheme. The controller is further configured to receive a selection of a value of a parameter that adjusts a number of differences between the dependency networks in accordance with the graphical modeling scheme. In turn, the modeling unit is configured to generate at least one version of the dependency networks based on the selected value of the parameter and to output the one or more versions of the dependency networks to permit a user to analyze distinctions between the dependency networks.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
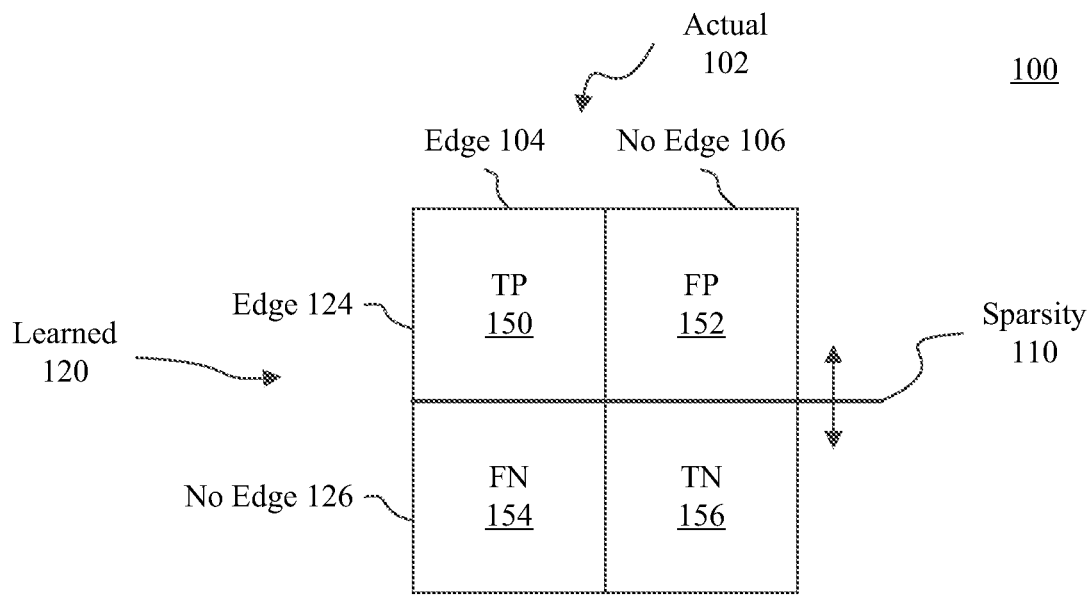
FIG. 1 is a diagram illustrating possible scenarios for identifying dependencies in a confusion matrix.

Exemplary embodiments of the present invention described herein provide an intuitive mechanism to control the quality of learned differences between dependency networks. In particular, preferred embodiments achieve an effective balance between ensuring a small number of spurious differences (precision) and identifying a large number of differences (recall). Transfer learning techniques are employed to control the precision-recall trade off in differential network analysis, and thereby significantly improve the quality of the learned differences. Transfer learning algorithms for graphical models focus on using inductive bias to produce networks that are similar to each other. Preferred embodiments use transfer learning to bias the learned dependency networks for the different tasks to be similar. The more heavily this bias is enforced, the fewer differences will be learned between tasks. The underlying thesis of this approach is that true differences that are well supported in the data will tend to need a higher bias to be eliminated, while spurious differences will be eliminated even with a small bias. Applying these techniques on oncological data, for example, with limited numbers of samples, identifies differential dependencies that provide insight into the changing interactions of proteins due to cancer. In neuroimaging data, these techniques can find visual processing pathways as well as insights into regions that relate to visual object recognition.

Preferred embodiments of the present invention infer and visualize sets of dependency networks for several input datasets and identify differences between the dependency networks. The preferred methods and systems use transfer learning to encourage similarities among the learned networks, thereby controlling the number of false differences discovered. As such, transfer learning is employed to obtain high quality differences. In particular, the preferred embodiments permit a user to easily and interactively explore tradeoffs between the number of differences identified between the networks and the confidence that these differences are real. Thus, they provide the user with two control mechanisms to control this analysis: one that controls the confidence in the learned edges of the networks, and one that controls the confidence in the identified differences. Accordingly, preferred embodiments provide a mechanism to control the precision-recall trade off in differential network analysis. In accordance with the methods and systems described here, users can explore dependency networks inferred from various sets of data and can change the values of the two control mechanisms and observe the resulting network structures. For example, the user can explore a network by selecting vertices or edges, zooming, panning, dragging subnetworks to change the layout, etc., and observe the effects of the changes that occur in the other networks. Users are also able to apply simple tools for network comparison to help visualize the similarities and differences among classes, such as color-coding the edges that are different between classes and those that are similar. Thus, preferred embodiments provide a user with the ability to infer and explore sets of dependency networks that display a relatively small, but highly confident, number differences between them. In particular, they permit a user to accurately determine how the phenomena that generated the datasets differ and thereby draw higher quality conclusions and theories about the phenomena.

It should be understood that embodiments described herein may be entirely hardware or may include both hardware and software elements, which includes but is not limited to firmware, resident software, microcode, etc. In a preferred embodiment, the present invention is implemented in hardware and software.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 2:
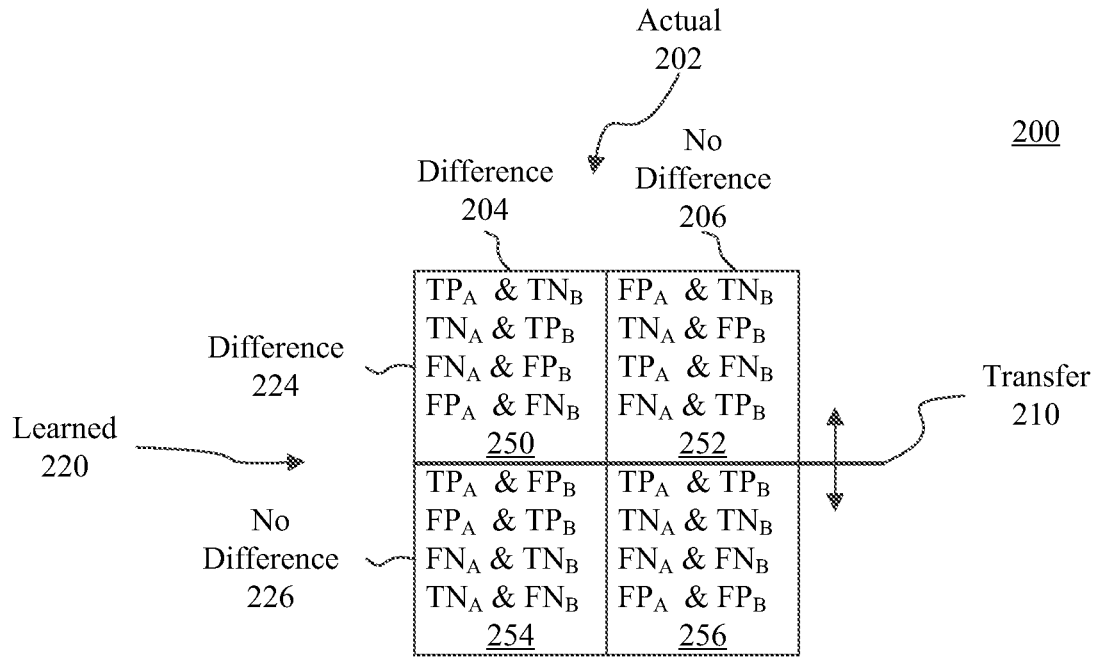
FIG. 2 is a diagram illustrating the possibilities for identifying differences between dependency networks that have been learned independently.

Referring now to the drawings in which like numerals represent the same or similar elements and initially to FIGS. 1 and 2, possibilities matrices for analyzing dependency networks are illustratively depicted. Data sets that form the bases of dependency networks, such as, for example, biological data, can contain hundreds or thousands of variables, but often only hundreds of samples. The data may be noisy and there may be some model mismatch. Thus, it should be assumed that there will be errors when learning dependency networks from data. When the networks are learned in isolation, errors in identifying edges are likely to be made independently, which, in turn, introduces spurious differences between learned networks. To illustrate this issue, the precision-recall tradeoff for identifying edges in individual networks is discussed. For example, FIG. 1 provides a diagram 100 illustrating the possible scenarios for identifying each dependency, or edge, in a confusion matrix. The horizontal axis 102 corresponds to an actual dependency network delineating edges 104 as well as no edges 106, while the vertical axis 120 corresponds to a learned dependency network delineating edges 124 and no edges 126. Ideally, all edges would be identified as true positives (TP) 150 or true negatives (TN) 156; however, this is not possible given limited data. Thus, there will also be some false positives (FP) 152 and false negatives (FN) 154. Sparse network learning algorithms, such as graphical lasso, aim to learn relatively few edges by increasing the degree of sparsity of the learned network. The learning algorithm has no control over the vertical line separating the actual edges from non-edges. However, by changing the sparsity parameter, the algorithm effectively moves the boundary 110 between the learned edges and non-edges. Assuming the algorithm is able to identify edges with better than random probability, then the precision (TP=(TP+FP)) will increase with sparsity; in turn, the recall (TP=(TP+FN)) will decrease.

While it may seem preferable to find the ideal sparsity level before comparing the networks, it has been found that there is no such ideal setting. In particular, it has been found that regardless of the setting of the sparsity parameter, there will be errors, and when errors are made independently for each dataset there will be many false differences. It can be shown that the likelihood of determining edges correctly in dependency networks that are learned independently is less likely than correctly determining an edge in a single network, rendering it even more difficult to learn differences than it is to learn individual edges. Regardless the dependency precision-recall tradeoff for each individually-learned network, a large number of false differences will be identified when the differences are learned independently.

FIG. 2 illustrates the possibilities for identifying differences between dependency networks in an example in which dependency networks have been learned independently. Here, the horizontal axis 202 corresponds to actual differences between two dependency networks delineating differences 204 as well as no differences 206, while the vertical axis 220 corresponds to a learned dependency network delineating differences 224 and no difference 226. The subscripts in blocks 250, 252, 254 and 256 denote to which of the two dependency networks, A or B, the list of true positives, true negatives, etc. correspond. To increase the precision of learned differences, the system should be able to adjust the horizontal boundary 210 between learned differences and non-differences. For learning edges in individual networks, this can be accomplished through the setting of the sparsity penalty. For learning multiple networks with few differences, the networks should be biased to be similar to each other. This type of bias is transfer learning. When learning multiple networks with transfer learning, the number of differences learned is decreased by increasing the transfer strength parameter. As a result, edges in both networks will tend to either be chosen together or left out together. In essence, only the differences that are strongly supported by the data will survive this bias, thereby providing a high confidence that those edges that are identified as differences are very likely to be true differences.

Thus, to identify high-precision differences, networks should be inferred together to facilitate comparison, rather than learning the networks in isolation and then comparing them to each other. To achieve this, a transfer learning technique, also called multitask learning (MTL), can be utilized. Specifically, preferred embodiments employ an MTL graphical lasso objective function that explicitly controls the number of differences learned.

Prior to describing the use of transfer learning to determine multiple networks, a standard model for learning a single network is described. Gaussian graphical models (GGMs) infer a network of conditional dependencies from multivariate data by approximating the inverse covariance matrix with a sparse solution. If X is a p-dimensional Gaussian random variable $X \sim \mathcal{N}(0,\Sigma)$, then $\Theta=\Sigma^{-1}$ is the precision matrix. Entries in the precision matrix are partial correlations, i.e. $\theta_{ij}$ is the correlation of variables $X_i$ and $X_j$ given all other variables $X_m$, $m \neq i, j$. A value of $\theta_{ij}=0$ implies conditional independence of $X_i$ and $X_j$. Therefore, the precision matrix can be interpreted as an undirected network where nodes are the variables in the precision matrix and edges connect variables with non-zero partial correlations.

The learning objective for a single network using GGMs here is $$\hat{\Theta} = \arg\max_{\Theta>0} \log\det\Theta - tr\left(\sum \Theta\right) - \lambda\|\Theta\|_1 \quad (1)$$

The parameter $\lambda$, $0 \leq \lambda \leq 1$, controls the degree of sparsity. Varying this parameter affects the precision recall tradeoff of identifying dependencies. Rather than selecting one particular value for $\lambda$, it is usually more informative to inspect the networks inferred at various values to see how edges appear/disappear along the precision-recall curve.

Often, the Gaussian assumption is too strong for real data. Extreme values in just a few samples, such as 1% of the data, can produce a large number of Gaussian correlations that do not exist when those samples are not present. Transelliptical models replace the Gaussian covariance matrix with a non-parametric correlation matrix which is far less sensitive to extreme values. Preferred embodiments use the Kendall's tau correlation based on rank-statistics. This is a nonparametric measure of correlation between pairs of variables.

To illustrate the use of Kendall's tau correlation, we define the Kendall's tau correlation coefficient between two random variables S and T as follows. Assume that $(s_1, t_1)$, $(s_2, t_2), \ldots, (s_n, t_n)$ are a set of observations of the joint random variables S and T respectively. Any pair $(s_i, t_i)$ and $(s_j, t_j)$ is concordant if both $s_i > s_j$ and $t_i > t_j$ or if both $s_i < s_j$ and $t_i < t_j$. In turn, if $s_i > s_j$ and $t_i < t_j$ or if $s_i < s_j$ and $t_i > t_j$, the pair is discordant. Further, if $s_i = s_j$ or $t_i = t_j$, the pair is neither concordant nor discordant. The Kendall $\tau$ coefficient is defined as:

$$\tau = \frac{(\text{number of concordant pairs}) - (\text{number of discordant pairs})}{\frac{1}{2}n(n-1)}$$

The (i,j) entry of the Kendall's $\tau$ correlation matrix of the multivariate variable $X=(X_1, \ldots, X_n)$ is the Kendall's $\tau$ correlation coefficient between variables $X_i$ and $X_j$.

To learn the transelliptical graphical model, the system can simply replace the sample inverse covariance matrix $\Sigma$ with the Kendall's tau correlation matrix in the graphical lasso objective function. This change makes the learning significantly more robust to outliers and non-gaussianity, without any significant loss in accuracy, even when data is truly Gaussian.

To learn multiple graphical models from multiple sets of data, preferred embodiments use the joint graphical lasso algorithm which incorporates a transfer bias term to encourage the learned networks to be similar. If we have k classes of data, we will estimate $\Sigma^k$ for each set of data and learn a sparse precision matrix, $\hat{\Theta}^k$, for each class of data by solving the following optimization function:

$$\max_{\Theta^k>0, \forall k} \sum_k [\log\det\Theta^k - tr(\Sigma^k\Theta^k)] - \lambda_1(1-\lambda_2)\|\Theta\|_1 - \lambda_1\lambda_2\sum_{i \neq j}\|\theta_{ij}\|_2 \quad (2)$$

Here, $\|\Theta\|_1$ is shorthand for the entry wise $L_1$ norm of all $\Theta^k$ and $\theta_{ij}$ is a k-dimensional vector of partial correlations between $X_i$ and $X_j$. The parameter $\lambda_1$ controls the degree of sparsity in much the same way as the $\lambda$ parameter in the single task case. There is also a parameter $\lambda_2$, $0 \leq \lambda_2 \leq 1$, that controls the number of differences learned among the tasks. When $\lambda_2=0$, the objective is the same as several independent single-task learning problems. As $\lambda_2$ approaches 1, the structures learned will be identical. Therefore, this parameter can be used to limit the number of differences learned. More importantly, the only differences that will survive this penalty term are those that are highly supported by the data. Table 1, below, provides pseudocode for a method for determining dependency networks based on equation (2).

TABLE 1

Psuedocode for determining dependency networks

Figure 3:
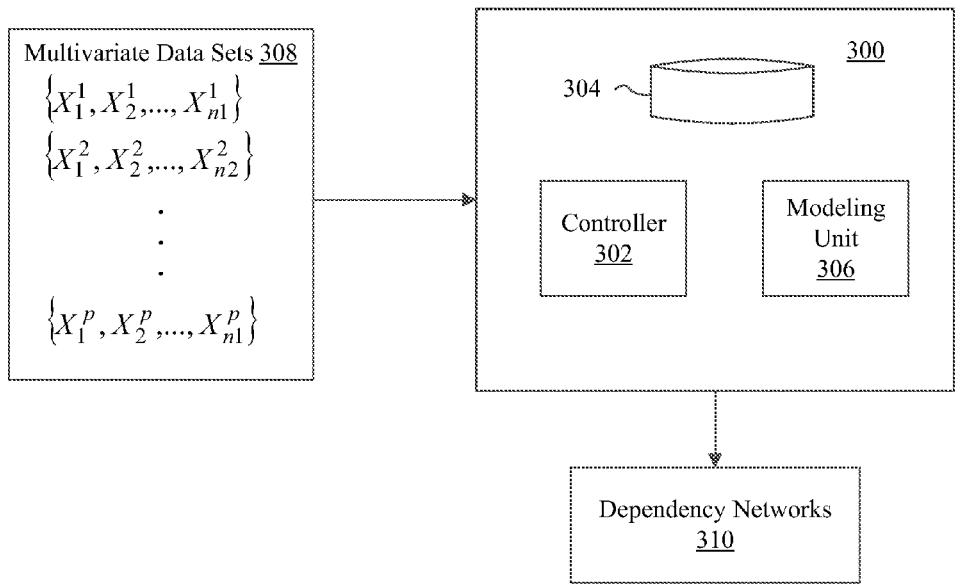
FIG. 3 is a high-level block/flow diagram of a system for displaying dependencies within data and illustrating differences between a plurality of data sets in accordance with an exemplary embodiment.
Figure 4:
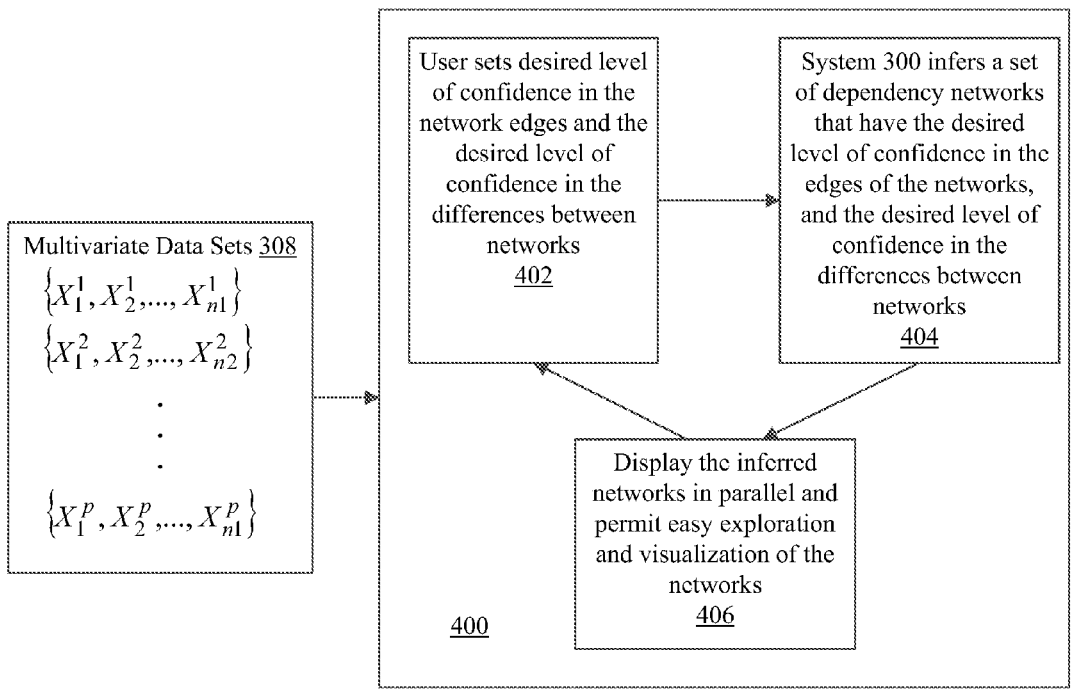
FIG. 4 is a high-level block/flow diagram illustrating a general overview of the processing that can be conducted by the system depicted in FIG. 3.

INPUT: Multivariate samples $\{X_1^1, X_2^1, \ldots, X_{n1}^1\}, \ldots \{X_1^K, X_2^K, \ldots, X_{nK}^K\}$ from K conditions
OUTPUT: K dependency networks, one for each condition
    FOR k from 1 to K do
        Calculate generalized correlation matrix $\Sigma^k$ from
        $\{X_1^k, X_2^k, \ldots, X_{nk}^k\}$ using Kendall's
            tau, Spearman correlation, or another correlation measure
    ENDFOR
    Use any convex optimization procedure to optimize the function eq. (2) above
    $\{\Theta^1, \Theta^2, \ldots, \Theta^K\} \leftarrow$ Solution of the optimization problem in eq. (2)
    FOR k from 1 to K do
        Generate dependency network k from $\Theta^k$
    ENDFOR Turning now to FIG. 3, a system 300 for displaying dependencies within data and illustrating differences between a plurality of data sets in accordance with an exemplary embodiment is illustratively depicted. The system 300 can include a controller 302, a modeling unit 306 and a storage medium 304. As discussed in more detail herein below, the controller 302 and the modeling unit 306 can be implemented by one or more processors executing software instructions stored on the storage medium 304. The system 300 can be configured to receive data sets 308 $\{X_1^1, X_2^1, \ldots, X_{n1}^1\}, \{X_1^2, X_2^2, \ldots, X_{n2}^2\}, \ldots \{X_1^K, X_2^K, \ldots, X_{nk}^K\}$ and generate dependency networks 310. For example, FIG. 4 illustrates a general overview 400 of the processing that can be conducted by system 300. Here, the system 300 can receive data sets 308, which can represent a variety of different data for multiple groups for which a user seeks to determine important differences. For example, the data sets can describe information for one or more populations that are infected with a disease, while one or more other data sets can describe data for healthy populations so that the system can permit the user to determine differences between the data sets. Examples of the data sets can include data concerning computing systems or networks, among other examples, as discussed in more detail herein below.

The system permits users to visualize dependency structures and permits users to easily explore the tradeoffs between the number of networks edges inferred and the number of differences between inferred networks, as well as the confidence that these edges and differences are real. In particular, the system 300 provides users with at least two parameters to control this analysis: one parameter that controls the confidence in the learned edges of the networks, and one parameter that controls the confidence in the identified differences. For example, the first parameter can be $\lambda_1$ while the second parameter can be $\lambda_2$, as discussed above with respect to equation (2). Thus, at block 402, a user may set a desired level of confidence in the network edges and the desired level of confidence in the differences between networks. The ability to control the confidence in both the identified differences and the identified network arcs is important for enabling the user to draw confident conclusions or specify clear theories based on the confidence in the differences between the dependency networks.

At block 404, the system 300 can infer a set of dependency networks that have the desired level of confidence in the edges of the networks, and the desired level of confidence in the differences between networks. As discussed above, the system 300 can use transfer learning to encourage similarities among the learned networks, thus controlling the number of false differences discovered. Here, higher confidence differences are those that appear when inferred networks are encouraged to be more similar to each other.

At block 406, the system 300 can display the inferred networks in parallel to permit easy exploration and visualization of the networks for the user. In particular, the system 300 enables users to explore the inferred networks and the differences among them using a visualization system. For example, the system enables a user to explore a network by selecting vertices or edges, zooming, panning, dragging subnetworks to change the layout, etc. . . . The system can be configured to present the same changes occurring in the other networks as a result of changing the confidence parameters, or any other changes the user makes to explore the network. In addition, the system enables users to apply simple tools for network comparison to help visualize the similarities and difference among networks, such as color-coding the edges that are different between classes and edges that are similar.

Figure 5:
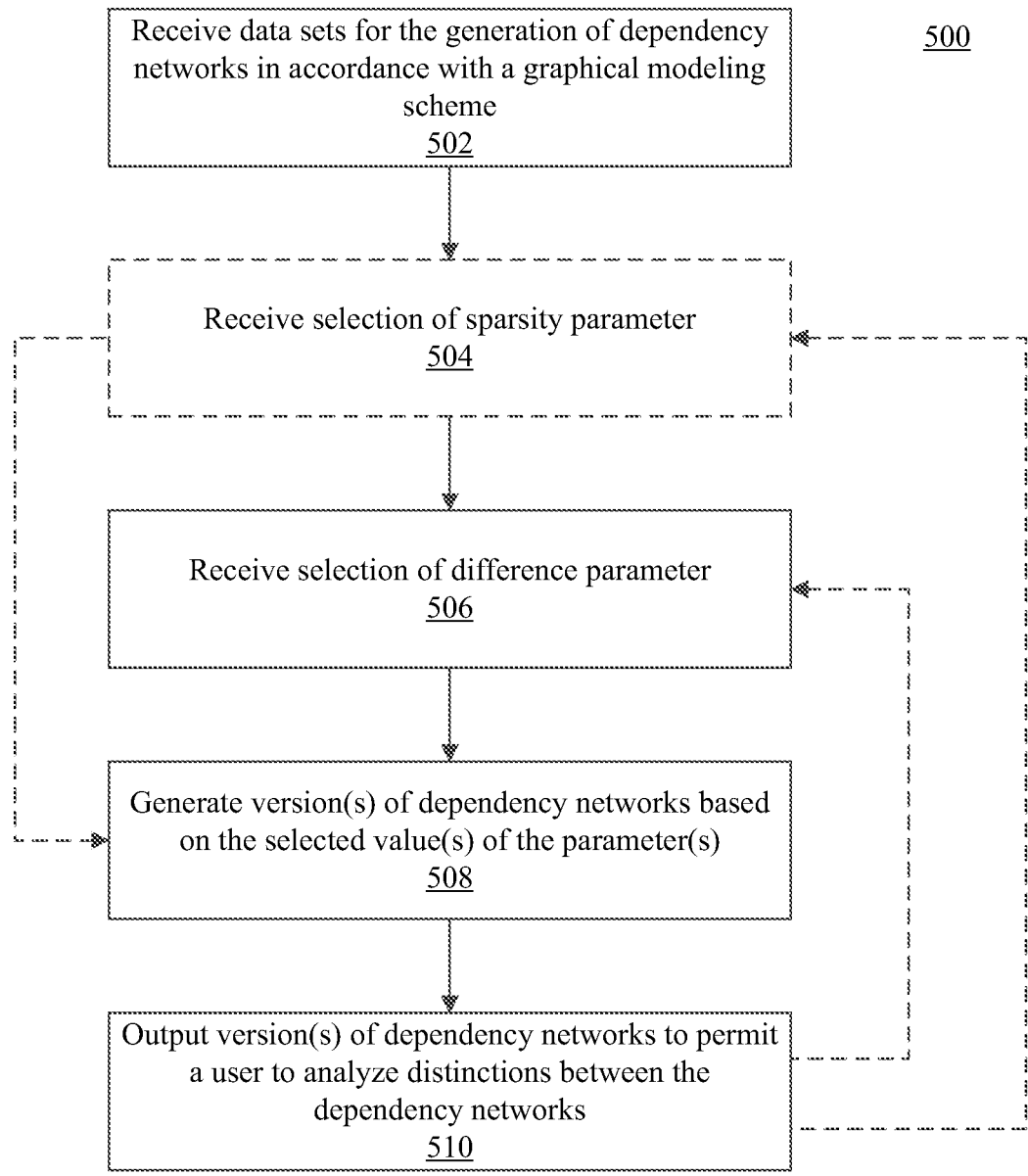
FIG. 5 is a high-level flow diagram of an exemplary method for displaying dependencies within data and illustrating differences between a plurality of data sets in accordance with an exemplary embodiment of the present invention.

To better illustrate features of the system 300, reference is made to FIG. 5, which depicts a method 500 for displaying dependencies within data and illustrating differences between a plurality of data sets in accordance with an exemplary embodiment of the present invention, which can be implemented by the system 300. The method 500 can begin at step 502, at which the controller 302 of the system 300 can receive the plurality of data sets for the generation of a plurality of dependency networks in accordance with a graphical modeling scheme. For example, the data sets can be data sets 308 described above. As discussed in more detail herein below, the data sets can be a wide assortment of different data. For example, the data sets can include one set of data describing measurements of gene expression levels in diseased tissue, while another data set can describe measurements of gene expression levels in healthy tissue for comparison purposes. Alternatively, the sets of data can include a set comprising functional magnetic resonance imaging (FMRI) scans from subjects suffering from a mental disorder, and another set including FMRI scans from healthy subjects. In addition, the data can also be related to computing data. For example, one data set can include computer or network system log data before a system modification is performed, while another data set can include computer or network system log data after a system modification is performed to enable a user to determine the effects that the modification will have on the system. The data sets provided to the system 300 can include a large assortment of different data for different analytical fields.

Optionally, at step 504, the controller 302 can receive a selection of a value of a parameter that adjusts a sparsity of edges within at least one of the dependency networks in accordance with the graphical modeling scheme. For example, the parameter can be $\lambda_1$, discussed above with respect to equation 2, where the user can select values of $\lambda_1$ ranging from $0 \leq \lambda_1 \leq 1$.

At step 506, the controller 302 can receive a selection of a value of a parameter that adjusts a number of differences between the dependency networks in accordance with the graphical modeling scheme. For example, the parameter can be $\lambda_2$, discussed above with respect to equation 2, where the user can select values of $\lambda_2$ ranging from $0 \leq \lambda_2 \leq 1$.

At step 508, the modeling unit 306 can generate at least one version of the dependency networks based on the selected value(s) of the parameter(s). For example, the modeling unit 306 can generate the one or more versions of the dependency networks based on the value received at step 504 and/or on the value received at step 506. Here, the dependency networks can be GGMs or, preferably are transelliptical graphical models, as discussed above. Further, the models can be precision matrices, where each entry of each of the matrices denotes whether a dependency exists between two given variables. For example, as discussed above, the precision matrix can be $\hat{\Theta}^k$ of equation (2) and can be found as discussed above for each dependency network/class of data k by employing a graphical lasso objective function. As indicated above, an advantage of employing transfer learning here is that the dependency networks are learned simultaneously, thereby reducing the number of spurious learned differences between the dependency networks.

Figure 6:
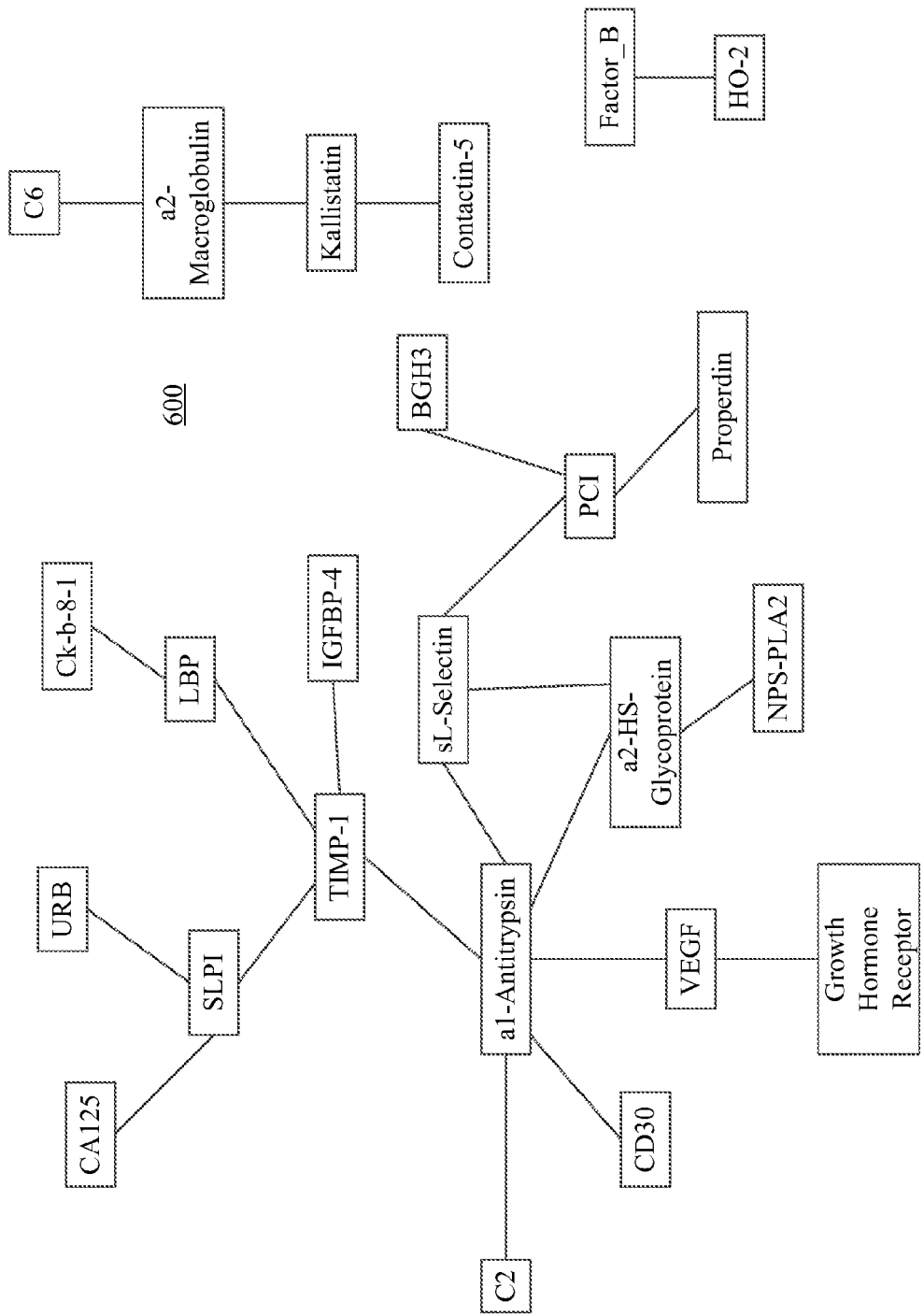
FIGS. 6 and 7 illustrate differential dependency networks that can be determined in accordance with exemplary embodiments of the present invention.
Figure 7:
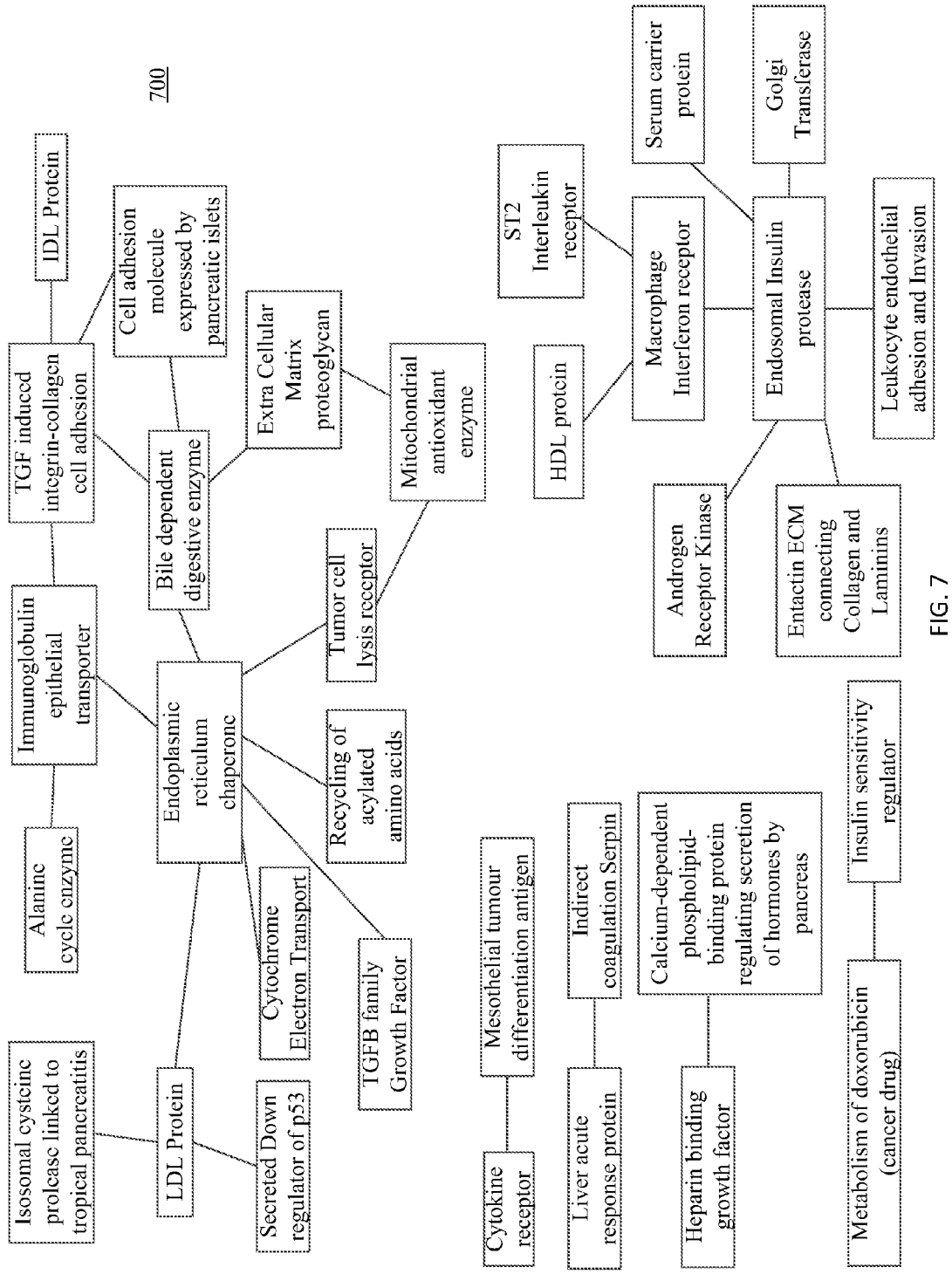

In accordance with one exemplary aspect, the versions generated by the modeling unit at step 508 can be respective graphical depictions of the precision matrices $\hat{\Theta}^k$. Alternatively, the modeling unit can generate a difference network as the version of the dependency networks. For example, the version can be configured such that only edges between variables that are different between dependency networks are illustrated. For example, for a cancer study in which the received data sets 308 include information describing infected populations and information describing control populations, FIG. 6 illustrates a differential dependency network 600 between the population that suffers from ovarian cancer and the control populations for a sparsity setting of $\lambda_1=0.6$ and a transfer setting of $\lambda_2=0.6$. Every edge or arc in this network represents a dependency that is present in the cancer population but not in the control population. Similarly, FIG. 7 illustrates an example of a pancreatic cancer difference network 700 between cancer and control populations for the sparsity setting $\lambda_1=0.6$ and the transfer setting $\lambda_2=0.6$, with the node labels showing the functional descriptions in lieu of the protein names.

At step 510, the modeling unit 306 can output the one or more versions of the dependency networks to permit a user to analyze distinctions between the dependency networks.

As noted above, the system 300 can permit a user to explore the precision-recall tradeoff by adjusting the sparsity parameter 2 and/or the transfer parameter $\lambda_2$. Thus, after outputting one or more versions of the dependency networks at step 510, the method 500 can proceed to step 504, at which the system can receive a selection of a sparsity parameter that is different from the selection previously received at step 504. Thereafter, the method can proceed to step 508, at which the modeling unit 306 can generate new version(s) of the dependency networks based on this newly received sparsity parameter and on the previously and most recently received transfer parameter. In addition, the system 300 can output the new version(s) at step 510, as discussed above.

Alternatively, as opposed to changing only the sparsity parameter $\lambda_1$, the user can change the transfer parameter $\lambda_2$. Here, after outputting one or more versions of the dependency networks at step 510, the method 500 can proceed to step 506, at which the system can receive a selection of a transfer parameter that is different from the selection previously received at step 506. Thereafter, the method can proceed to step 508, at which the modeling unit 306 can generate new version(s) of the dependency networks based on this newly received transfer parameter and on the previously and most recently received sparsity parameter.

Alternatively, as opposed to changing only one of the parameters $\lambda_1$, $\lambda_2$, the user can change both of the parameters. Here, after outputting one or more versions of the dependency networks at step 510, the method 500 can proceed to step 504, at which the system can receive a selection of a sparsity parameter $\lambda_i$ that is different from the selection previously received at step 504. Thereafter, the method can proceed to step 506, at which the system can receive a selection of a transfer parameter that is different from the selection previously received at step 506. Then, at step 508 the modeling unit 306 can generate new version(s) of the dependency networks based on the newly received sparsity and transfer parameters.

Figure 8:
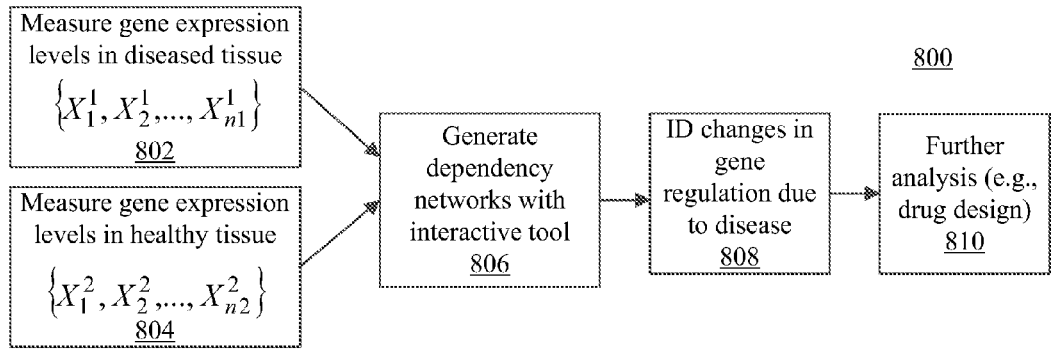
FIGS. 8-10 are high-level block/flow diagrams illustrating various applications of exemplary method and system embodiments of the present invention.
Figure 9:
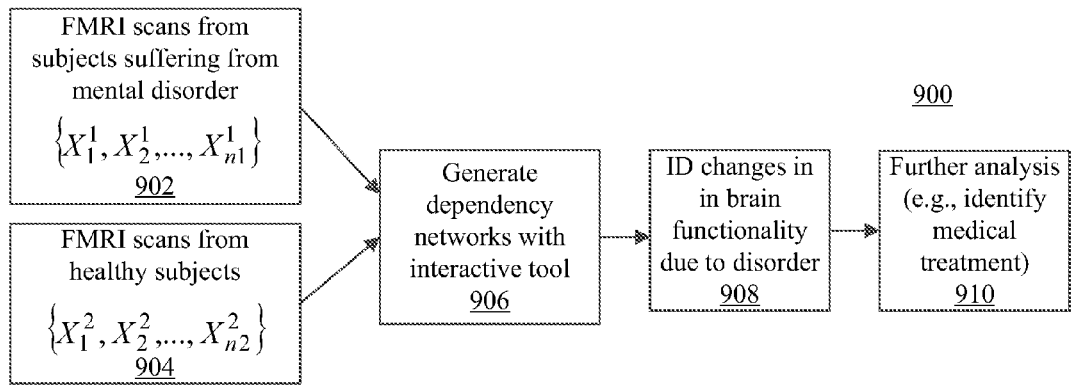
Figure 10:
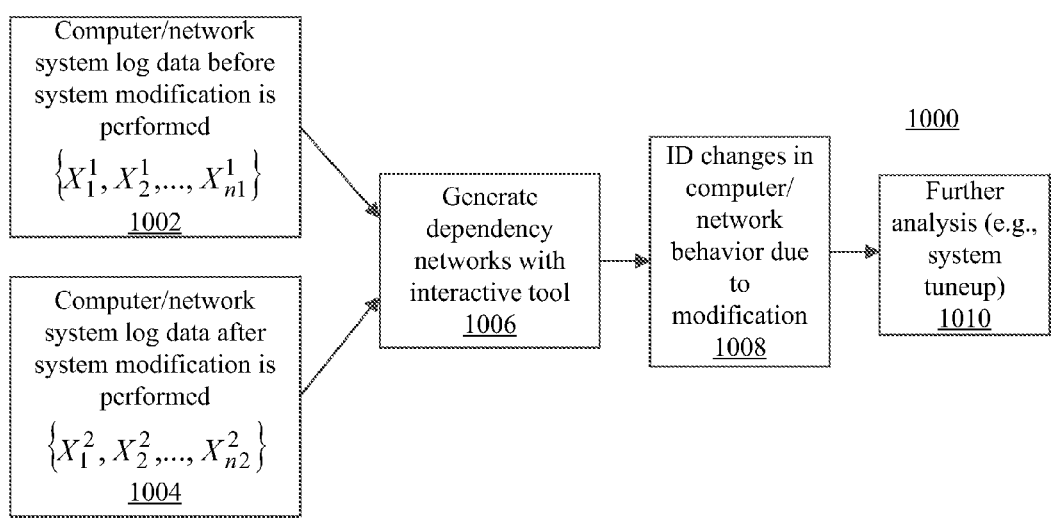

With reference now to FIGS. 8-10, flow diagrams illustrating various applications of the system 300 and the method 500 are depicted. It should be noted that these examples are not exclusive, as the system and method can be applied in many other settings. FIG. 8 illustrates a diagram 800 exemplifying the use of the system 300 for identifying changes in gene regulation in cancerous tissue. The gene expression levels are measured for cancerous tissue at block 802 and are measured for healthy tissue at block 804. The user can then employ the system 300 to generate the dependency networks at block 806, to infer and explore the dependency networks between the gene expression levels for the two tissue types, and to discover significant differences between the dependency network for cancerous tissue and the dependency network for healthy tissue. The differences in dependency networks can then be used to identify changes in gene regulation due to cancer at block 808. Additional steps, such as designing new drugs, can be taken at block 810.

FIG. 9 illustrates a diagram 900 exemplifying the use of the system 300 for identifying changes in brain functionality due to mental disorders. For example, FMRI scans can be collected for subjects suffering from a mental disorder, such as schizophrenia, at block 902 and for healthy subjects at block 904. The user can then employ the system 300 to generate dependency networks at block 906 to permit users to explore the dependency networks between the FMRI voxel activations for the two subject populations, and to discover significant differences between the dependency network for subjects suffering from a mental disorder and the dependency network for healthy subjects. The differences in dependency networks can then be used, at block 908, to identify changes in brain functionality due to the disease. Further steps, such as, for example, designing medical treatment, can be taken at block 910.

FIG. 10 illustrates a diagram 1000 exemplifying the use of the system 300 for identifying and monitoring the effects of changes made to a computer/network system. For example, system logs can be taken before a system modification is implemented at block 1002 and after the system modification is implemented at block 1004. The system 300 can then be used to generate the dependency networks at block 1006 to permit a user to explore the dependency networks between measurements of the computer/network system (e.g. CPU activity, network traffic, network latency, memory usage, etc.) before and after the system change is implemented, and to discover significant differences between the dependency network before the system change is implemented and the dependency network after the system change is implemented. The differences in the dependency networks can then be used to identify effects of the system modification at block 1008. Further steps, such as system tune-ups, can be taken at block 1010.

Thus, exemplary embodiments of the present invention described herein provide a user with the ability to specify a desired level of confidence in the inferred differences between the dependency networks. The system enables the user to interactively explore the differences inferred at various confidence levels and draw confident conclusions or specify clear theories based on the confidence in the differences between the dependency networks.

Figure 11:
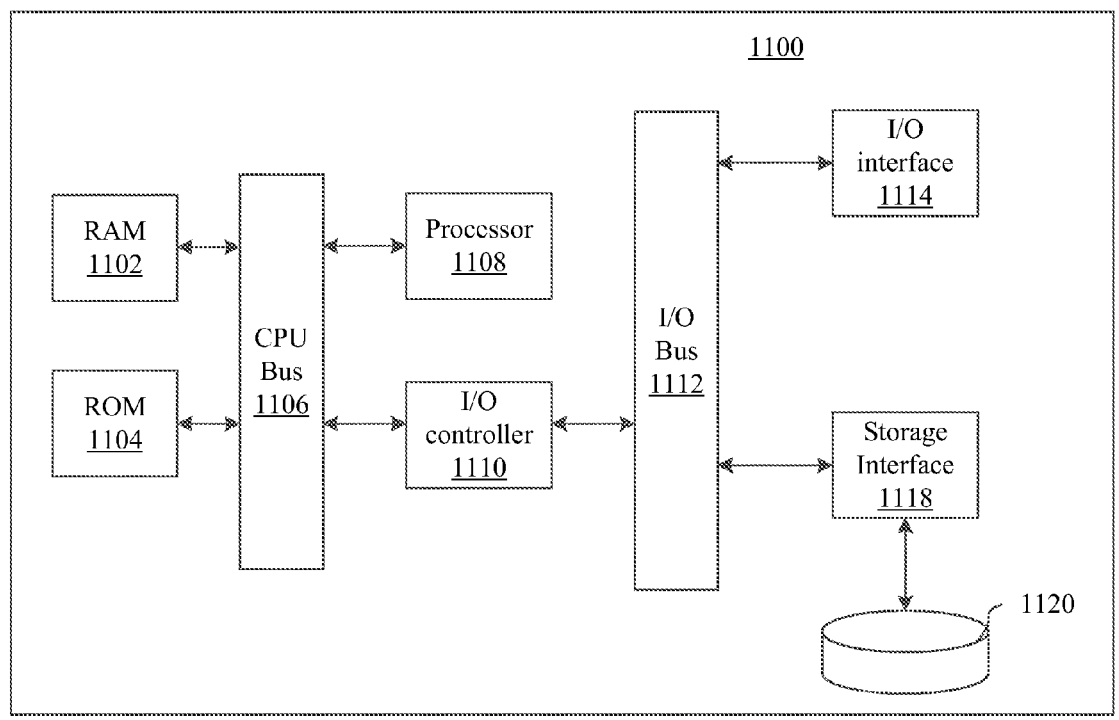
FIG. 11 is a high-level block diagram of a computing system by which exemplary method and system embodiments of the present invention can be implemented.

Referring now to FIG. 11, an exemplary computing system 1100 in which system embodiments of the present principles described above can be implemented, and by which method embodiments of the present principles described above can be implemented, is illustrated. The computing system 1100 includes a hardware processor 1108 that can access random access memory 1102 and read only memory 1104 through a central processing unit bus 1106. In addition, the processor 1108 can also access a storage medium 1120 through an input/output controller 1110, an input/output bus 1112 and a storage interface 1118, as illustrated in FIG. 11. The system 1100 can also include an input/output interface 1114, which can be coupled to a keyboard, mouse, touch screen, external drives or storage mediums, display device, etc., for the input and output of data to and from the system 1100. In accordance with one exemplary embodiment, the processor 1108 can access software instructions stored in the storage medium 1120 and can access memories 1102 and 1104 to run the software and thereby implement the method 500 described above. In addition, the hardware processor 1108 can, for example by executing software instructions stored on the storage medium 1120, implement system elements described above, such as the controller 302 and the modeling unit 306. Alternatively, each of these system elements can be implemented via a plurality of respective processors 1108. Further, the data sets, versions of dependency networks 310 generated by the system 300, as well as any data used to generate the versions, can be stored in the storage medium 1120, which is one implementation of the storage medium 304. Additionally, the input/output interface 1114 can be employed to receive data sets 308 and selections of parameters $\lambda_1$ and/or $\lambda_2$ from a user and/or to output and illustrate versions of the dependency networks 310 generated by the system 300 for the user. Alternatively or additionally, the versions of the dependency networks can be stored in the storage medium 1020 for subsequent retrieval by a user.

Having described preferred embodiments of methods and systems for dependency network analysis (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for displaying dependencies within data and illustrating differences between a plurality of data sets comprising:

receiving the plurality of data sets for generation of a plurality of dependency networks in accordance with a graphical modeling scheme:

receiving a selection of a value of a parameter that adjusts a number of differences between the dependency networks in accordance with said graphical modeling scheme;

generating, by a hardware processor, at least one version of said dependency networks based on the selected value of the parameter;

outputting said at least one version of said dependency networks to permit a user to analyze distinctions between said dependency networks;

wherein said dependency networks are inferred together to facilitate comparison through the utilization of a multitask learning (MTL) transfer learning technique wherein the networks are biased to be similar to each other; and wherein the graphical modeling scheme is based on a graphical lasso objective function that explicitly controls the number of differences learned and incorporates a transfer bias term.

2. The method of claim 1, wherein said selection is a first selection, said first value is a first value, said at least one version is at least one first version and said method further comprises:

receiving a second selection of a second value of said parameter;

generating at least one second version of said dependency networks based on the selected second value of the parameter; and outputting said at least one second version of said dependency networks to permit the user to analyze the distinctions between said dependency networks based on said at least one first version and of said at least one second version.

3. The method of claim 1 wherein said selection is a first selection, said value is a first value, said parameter is a first parameter and wherein said method further comprises:

receiving a second selection of a second value of a second parameter that adjusts a sparsity of edges within at least one of the dependency networks in accordance with said graphical modeling scheme, wherein said generating further comprises generating said at least one version of said dependency networks based on the selected second value of the second parameter.

4. The method of claim 3, wherein said at least one version is at least one first version and said method further comprises:

receiving a third selection of a third value of said first parameter and a fourth selection of a fourth value of said second parameter;

generating at least one second version of said dependency networks based on the selected third value of the first parameter and the selected fourth value of said second parameter; and outputting said at least one second version of said dependency networks to permit the user to analyze the distinctions between said dependency networks based on said at least one first version and said at least one second version.

5. The method of claim 1, wherein said dependency networks are transelliptical graphical models.

6. The method of claim 5, wherein said models are precision matrices and wherein each entry of each matrices denotes whether a dependency exists between two given variables.

7. The method according to claim 1 wherein for k classes of data, an estimate $\Sigma^k$ for each set of data is made and a sparse precision matrix $\ddot{\Theta}^k$ is learned for each class of data by solving the following optimization function:

$$\max_{\Theta^k > 0, \forall k} \sum_k \left[ \log \det \Theta^k - tr\left(\sum^k \Theta^k\right) \right] - \lambda_1(1-\lambda_2) \|\Theta\|_1 - \lambda_1 \lambda_2 \sum_{i \ne j} \|\Theta_{ij}\|_2$$

where $\|\Theta\|_1$ is shorthand for entry wise $L_1$ norm of all $\Theta^k$, $\Theta_{ij}$ is k-dimensional vector of partial correlations between data sets $X_i$ and $X_j$, $\lambda_1$ controls the degree of sparsity, and $\lambda_2$, $0 \le \lambda_2 \le 1$, that controls the number of differences learned.

8. A method for displaying dependencies within data and illustrating differences between a plurality of data sets comprising:
receiving the plurality of data sets for generation of a plurality of dependency networks in accordance with a graphical modeling scheme;
receiving a first selection of a first value of a first parameter that adjusts a number of differences between the dependency networks in accordance with said graphical modeling scheme and a second selection of a second value of a second parameter that adjusts a sparsity within at least one of the dependency networks in accordance with said graphical modeling scheme;
generating, by a hardware processor, at least one version of said plurality of dependency networks based on the selected first value of the first parameter and on the selected second value of the second parameter;
outputting said at last one version of said plurality of dependency networks to permit a user to analyze distinctions between said dependency networks;
wherein said dependency networks are inferred together to facilitate comparison through the utilization of a multitask learning (MTL) transfer learning technique wherein the networks are biased to be similar to each other; and
wherein the graphical modeling scheme is based on a joint graphical lasso objective function that explicitly controls the number of differences learned and incorporates a transfer bias term.

9. The method of claim 8, wherein said at least one version is at least one first version and said method further comprises:
receiving a third selection of a third value of said first parameter and a fourth selection of a fourth value of said second parameter;
generating at least one second version of said plurality of dependency networks based on the selected third value of the first parameter and the selected fourth value of said second parameter; and
outputting said at least one second version of said plurality of dependency networks to permit the user to analyze the distinctions between said dependency networks based on said at least one first version and on said at least one second version.

10. The method of claim 8, wherein said dependency networks are transelliptical graphical models.

11. The method of claim 10, wherein said models are precision matrices and wherein each entry of each matrices denotes whether a dependency exists between two given variables.

12. The method according to claim 8 wherein for k classes of data, an estimate $\Sigma^k$ for each set of data is made and a sparse precision matrix $\ddot{\Theta}^k$ is learned for each class of data by solving the following optimization function:

$$\max_{\Theta^k > 0, \forall k} \sum_k \left[ \log \det \Theta^k - tr\left(\sum^k \Theta^k\right) \right] - \lambda_1(1-\lambda_2) \|\Theta\|_1 - \lambda_1 \lambda_2 \sum_{i \ne j} \|\Theta_{ij}\|_2$$

where $\|\Theta\|_1$ is shorthand for entry wise $L_1$ norm of all $\Theta^k$, $\Theta_{ij}$ is a k-dimensional vector of partial correlations between data sets $X_i$ and $X_j$, $\lambda_1$ controls the degree of sparsity, and $\lambda_2$, $0 \le \lambda_2 \le 1$, that controls the number of differences learned.

13. A system for displaying dependencies within data and illustrating differences between a plurality of data sets comprising:
a controller configured to receive the plurality of data sets for generation of a plurality of dependency networks in accordance with a graphical modeling scheme and to receive a selection of a value of a parameter that adjusts a number of differences between the dependency networks in accordance with said graphical modeling scheme; and
a modeling unit, implemented by a hardware processor, configured to generate at least one version of said dependency networks based on the selected value of the parameter and to output said at least one version of said dependency networks to permit a user to analyze distinctions between said dependency networks;
wherein said dependency networks are inferred together to facilitate comparison through the utilization of a multitask learning (MTL) transfer learning technique wherein the networks are biased to be similar to each other; and
wherein the graphical modeling scheme is based on a joint graphical lasso objective function that explicitly controls the number of differences learned and incorporates a transfer bias term.

14. The system of claim 13, wherein said selection is a first selection, said value is a first value, and said at least one version is at least one first version wherein said controller is further configured to receive a second selection of a second value of said parameter, and wherein said modeling unit is configured to generate at least one second version of said dependency networks based on the selected second value of the parameter and to output said at least one second version of said dependency networks to permit the user to analyze the distinctions between said dependency networks based on said at least one first version and of said at least one second version.

15. The system of claim 13, wherein said selection is a first selection, said value is a first value, said parameter is a first parameter and said controller is further configured to receive a second selection of a second value of a second parameter that adjusts a sparsity within at least one of the dependency networks in accordance with said graphical modeling scheme, and wherein said modeling unit is further configured to generate said at least one version of said dependency networks based on the selected second value of the second parameter.

16. The system of claim 15, wherein said sparsity is a sparsity of edges.

17. The system of claim 15, wherein said at least one version is at least one first version, wherein said controller is further configured to receive a third selection of a third value of said first parameter and a fourth selection of a fourth value of said second parameter, and wherein said modeling unit is further configured to generate at least one second version of said dependency networks based on the selected third value of the first parameter and the selected fourth value of said second parameter and to output said at least one second version of said dependency networks to permit the user to analyze the distinctions between said dependency networks based on said at least one first version and said at least one second version.

18. The system of claim 13, wherein said dependency networks are transelliptical graphical models.

19. The system of claim 18, wherein said models are precision matrices and wherein each entry of each of said matrices denotes whether a dependency exists between two given variables.

20. The system according to claim 13 wherein for k classes of data, an estimate $\Sigma^k$ for each set of data is made and a sparse precision matrix $\ddot{\Theta}^k$ is learned for each class of data by solving the following optimization function:

$$\max_{\Theta^k \succ 0, \forall k} \sum_k \left[ \log \det \Theta^k - tr\left(\sum^k \Theta^k\right)\right] - \lambda_1(1-\lambda_2)\|\Theta\|_1 - \lambda_1\lambda_2 \sum_{i \neq j} \|\Theta_{ij}\|_2$$

where $\|\Theta\|_1$ is shorthand for entry wise $L_1$ norm of all $\Theta^k$, $\Theta_{ij}$ is a k-dimensional vector of partial correlations between data sets $X_i$ and $X_j$, $\lambda_1$ controls the degree of sparsity, and $\lambda_2$, $0 \leq \lambda_2 \leq 1$, that controls the number of differences learned.

* * * * *